(12) United States Patent
Loftus et al.

(10) Patent No.: US 6,755,530 B1
(45) Date of Patent: Jun. 29, 2004

(54) RETINAL LIGHT PROCESSING USING CARBON NANOTUBES

(75) Inventors: David J. Loftus, Palo Alto, CA (US); Theodore Leng, Mountain View, CA (US); Harvey Fishman, Menlo Park, CA (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 94 days.

(21) Appl. No.: 10/198,672

(22) Filed: Jul. 16, 2002

(51) Int. Cl.$^7$ ............................. A61B 3/00; A61F 2/14; A61F 2/16; A61N 1/08; A61N 1/18

(52) U.S. Cl. ..................... 351/246; 351/200; 623/4.1; 623/6.63; 607/53; 607/54

(58) Field of Search ................................ 351/200, 205, 351/211, 246; 623/4.1, 6.63, 24, 25; 607/53, 54

(56) References Cited

U.S. PATENT DOCUMENTS

| | | | | |
|---|---|---|---|---|
| 5,024,223 A | * | 6/1991 | Chow ........................... | 607/53 |
| 5,556,423 A | * | 9/1996 | Chow et al. ................. | 623/6.63 |
| 5,865,839 A | * | 2/1999 | Doorish ....................... | 623/6.63 |
| 6,298,270 B1 | * | 10/2001 | Nisch et al. ................. | 607/54 |
| 2002/0161417 A1 | * | 10/2002 | Scribner ....................... | 607/54 |

OTHER PUBLICATIONS

S. Iijima, "Helical microtubules of graphitic carbon", Ltrs. to Nature, vol. 354 (Nov. 1991) pp. 87–89.
David H. Hubel, *Eye, Brain And Vision*, Scientific American Publ., New York, 1988, 1995, pp. 36–57.
Neil R. Miller et al, *Walsh & Hoyt's Clinical Neuro–Opthalmology*, Lippincott, Williams & Wilkins, Philadelphia, 1999, pp. 60–76.

* cited by examiner

Primary Examiner—Dennis W. Ruhl
Assistant Examiner—John R Sanders
(74) Attorney, Agent, or Firm—Robert M. Padilla; John F. Schipper (57) ABSTRACT

Method and system for processing light signals received by the eye of a human or other animal, where the eye may be compromised or non-functioning. Incident light is received at first and second pixels in a photodetector array and provides a pixel electrical signal representing the received light. Each of an array of carbon nanotube (CNT) towers is connected to a pixel, has a first tower end penetrating a retinal active layer of the animal and has a second tower end positioned to receive to receive and transport the pixel electrical signal to the retinal active layer. The CNT tower may be coated with a biologically active substance or chemically modified to promote neurite connections with the tower. The photoreceptor array can be provide with a signal altering mechanism that alters at least one of light intensity and wavelength intensity sensed by a first pixel relative to a second pixel, to correct for one or more selected eye problems.

34 Claims, 8 Drawing Sheets

Scale bar 100 μm

FIG. 8

RETINAL LIGHT PROCESSING USING CARBON NANOTUBES

FIELD OF THE INVENTION

This invention relates to receipt and processing of light signals by electronic apparatus associated with the eye.

BACKGROUND OF THE INVENTION

Diseases of, or damage to, the eye, such as macular degeneration and retinitis pigmentosa, often interfere with normal sight by compromising or destroying one or two components of the eye and leaving other components relatively untouched. Where this occurs, normal sight in an eye might be restored by providing a mechanism that provides an action equivalent to that of the compromised or destroyed component(s) and thereby restores overall functionality of the eye. However, application of this approach to the eye has proved hard to achieve, because of the nature of the components whose action must be restored and because the mechanism must be compatible with, but not interfere with, the eye's normal operation.

What is needed is an approach that provides an alternate path for light signal sensing on a pixel-size scale and that is small enough to be fitted within, or adjacent to, the compromised eye. Preferably, the approach should provide wavelength-sensitive light signal processing and should be flexible enough to allow signal processing changes that account for a changed visual environment. In addition, the approach should also allow analyses to improve an understanding of the eye's processing and integration of light signals, as well as changes in the processing and integration functions that may occur in response to diseases and other environmental perturbations.

SUMMARY OF THE INVENTION

These needs are met by the invention, which provides a system that receives, and identifies the site of receipt of, light on a pixel-size scale, delivers an electrical signal indicating this localized receipt of the light to an active layer of a subject's eye that normally receives and processes such localized signals, and thereafter utilizes the eye's signal processing system to provide an image that can be recognized by the subject. The invention may be applied to the eye(s) of a human or any other animal that has a similar visual system.

In one embodiment, the invention includes one or more carbon nanotube (CNT) towers, with each CNT tower including one or more CNTs, preferably multi-wall carbon nanotubes (MWCNTs). Each CNT tower has a first (exposed) end that penetrates the subject's retina from a sub-retinal or epi-retinal location to a depth of 25–200 microns ($\mu$m) and is located in a ganglion sub-layer or in a bipolar sub-layer (referred to collectively as the "active" layer) of the retina, in order to transfer an electronic or electromagnetic signal from the CNT tower to the contiguous layer of the retina for subsequent signal processing by the subject's eye. A second end of the CNT tower is connected through a metallic CNT growth catalyst (e.g., Fe, Ni, Co and/or Mo) and through a metallic underlayer or support layer (e.g., Al and/or Ir) to one or more of an array of light-receiving pixels in a photoreceptor array (e.g., a CCD pixel array). Each pixel has a preferred diameter of no more than about 50 nm, and preferably no larger than about 20 nm. The pixel array receives light that varies with pixel location on the array, and each pixel provides an electrical (electronic or electromagnetic) signal that is transferred through one or more CNT towers to the active layer of the retina. This system uses one or more CNT towers to transfer electrical signals from individual pixels in a pixel array to selected locations in an active layer of the retina.

In another embodiment, extension of neurite connections from the active layer of the retina to provide contact points for the CNT tower is encouraged, through chemical modification of, or provision of a selected coating of one or more proteins, growth factors and/or other biologically active substances on, a portion of the tower near the first end, or along the entire length of the tower.

In 1991, S. Iijima (Nature, vol. 354 pp. 56–58) reported growth of multi-wall coaxial nanotubes, containing 2–50 layers with radial separations of about 0.34 nm, using an arc discharge evaporation method similar to that used for Fullerene synthesis. The nanotubes originally observed by Iijima were formed on the negative voltage end of a carbon electrode and were plentiful in some regions and sparse in other regions. Since that time, other workers have developed other discharge means for controlled deposition of graphitic carbon.

Multi-wall carbon nanotubes (MWCNTs), single wall carbon nanotubes (SWCNTs) and carbon nanofibers (CNFs) have many potential applications that rely upon the large mechanical strength and/or large electrical conductivity associated with these structures, if the patterning of such structures can be controlled. Some workers have used liquid catalysts to initiate growth of some carbon nanotubes, but patterning of a finely detailed array of such structures is difficult using a liquid or a solid.

An array of CNTs can be grown by providing a substrate coated with an optional first thickness (preferably at least 1–10 nm) of a metal underlayer (e.g., Al or Ir or a mixture thereof) and with a second thickness (preferably at least 0.1–5 nm) of one or more active catalysts (e.g., Fe, Co, Ni and/or Mo, or a mixture thereof). A selected heated hydrocarbon gas (e.g., $CH_4$, $C_2H_4$, and/or $C_2H_2$) or intermediate species ($C_mH_n$) is passed over the coated substrate to successively strip the H atoms and deposit the carbon particles on the catalyst. Optionally, the underlayer includes a first sub-underlayer and a second sub-underlayer with different materials. For an SWCNT array, the preferred gas is $CH_4$ and the preferred temperature range is 800–1100° C. (preferably, T$\approx$900° C.) For an MWCNT array, the preferred gas is $C_2H_4$ or $C_2H_2$, the preferred temperature range is 650–900° C. (preferably, T$\approx$750° C.), and the Al or Ir underlayer is present. For a CNF array, a plasma discharge can be used to grow CNFs at T=400–900° C. (preferably, T$\approx$400–700° C.). A selected pattern for the metal sub-layers on the substrate, or of catalyst on the substrate coated with the metal sub-layer, is formed, using an apertured mask, and the carbon nanotubes are grown in the selected pattern. Size of the pattern can be as small as 20 nm, if electron beam lithography or ion beam sputtering is used to define the pattern.

DESCRIPTION OF BEST MODES OF THE INVENTION

Figure 1:
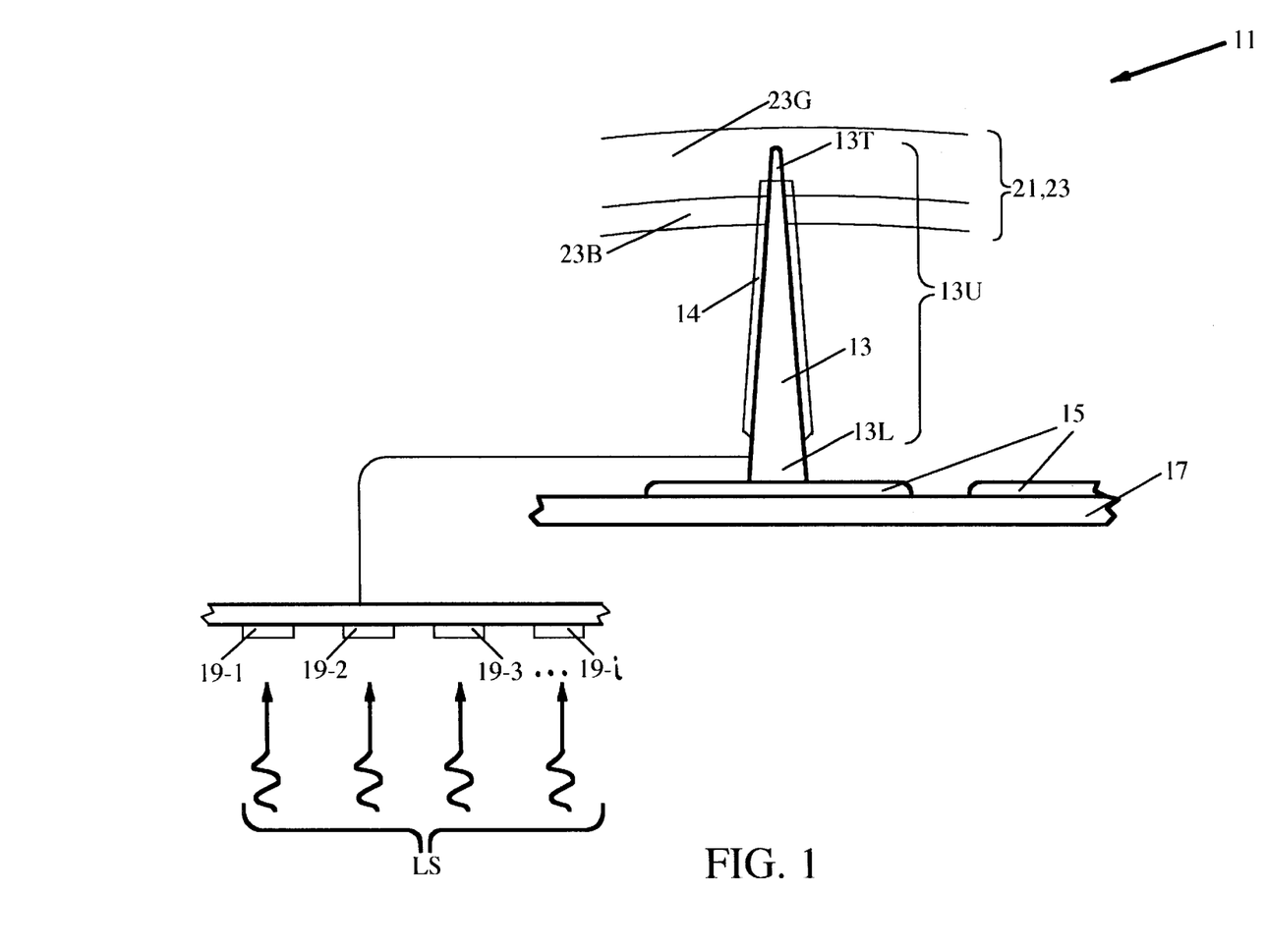
FIGS. 1 and 2 are schematic views of CNT towers, a CCD array of pixels and an active layer of the retina according to an embodiment of the invention.

FIG. 1 illustrates a system 11 for practicing the invention. The system 11 includes an array 13 of two or more CNT towers 13-j (j=1, . . . , J), with each tower including an assembly of one or more single wall or multi-wall CNTs, a catalyst layer 15 and a metal underlayer 17 to promote growth of the CNT towers, and a CCD array 19 of pixels 19-i (i=1, 2, . . . , I; I>2), which receives and electronically processes a location-dependent light signal LS. Arrangement of the CNT towers within the array may be hexagonal, rectangular or more generally polygonal. The spaces between the CNT towers can be uniform or non-uniform, commensurate with the requirements of the region of the retina in which the system operates.

A CNT tower 13 has a first (exposed) end 13U that is positioned to penetrate a retina 21 so that the first CNT tower end is located in a ganglion sub-layer 23G or in a bipolar sub-layer 23B of an active layer 23 of the retina. The CNT tower 13 has a second end 13L that is contiguous to the catalyst layer 15 (preferably Fe, Ni, Co and/or Mo), having a catalyst layer depth that is at least 0.1–5 nm, located on a metal underlayer 17 (preferably Al and/or Ir), having a depth of at least 1–20 nm, or more if desired. The catalyst layer 15 and the metal underlayer 17 promote growth of single wall and/or multi-wall CNTs and/or nanofibers (NFs) that preferably provide a CNT tower height of at least 25–200 $\mu$m (0.025–0.2 mm), with an active layer penetration depth of 25–200 $\mu$m.

A CNT tower 13-j preferably projects approximately perpendicularly from a surface of the catalyst 15. A portion of the CNT tower 13-j is optionally insulated and is intended to provide electrical isolation between an electrical system associated with the underlayer 17 and the retina 21. Preferably, each CNT tower 13-j has sufficient mechanical strength to penetrate the retina 21, from the anterior side (epi-retinal) or from the posterior side (sub-retinal), so that the first end 13U of the tower is accurately located within the ganglion sub-layer 23G or within the bipolar sub-layer 23B. Optionally, a portion of the CNT tower 13-j adjacent to, but not including, a tip 13T at the tower first end, is coated with an electrically insulating layer 14 so that, when the tower receives a signal from a CCD pixel 19-i, only the sub-layer, 23G or 23B, in which the tip is located will be stimulated electrically. The insulating layer 14 may also provide a strengthening of the junction between a CNT tower and the contiguous catalyst layer.

Figure 2:
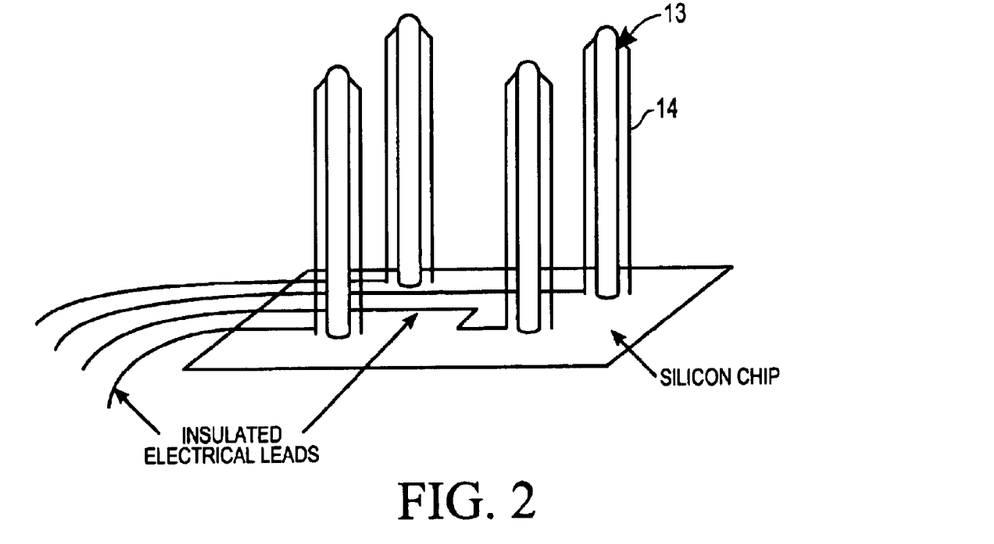

FIG. 2 is a perspective view illustrating four CNT towers projecting from a catalyst surface, with an insulated electrical lead running from each of the CNT towers to a CCD array (not shown in FIG. 2). The CNT towers and catalyst layer and under layer are preferably located on a silicon chip that has a selected microcircuit pattern. The microcircuit pattern can be laid down using ion beam sputtering or another suitable fabrication technique. CNT tower growth on the catalyst layer and the underlayer is implemented using chemical vapor deposition or another suitable growth method.

A CNT tower 13-j is connected to, and serves as an electrical pathway for signals provided by, the CCD array 19 of pixels 19-i. Each pixel 19-i in the array 19 receives and responds independently to light from a portion of an incident light signal LS, with the response depending upon the portion of the incident light signal that is received at the corresponding pixel (19-2 in FIG. 1). The amplitude and/or phase of the incident light signal LS can vary from one location on the photoreceptor array to another. Optionally, the system 11 in FIG. 1, including the CCD array 19, is implantable within or adjacent to the eye, in a sub-retinal or epi-retinal location.

Figure 3:
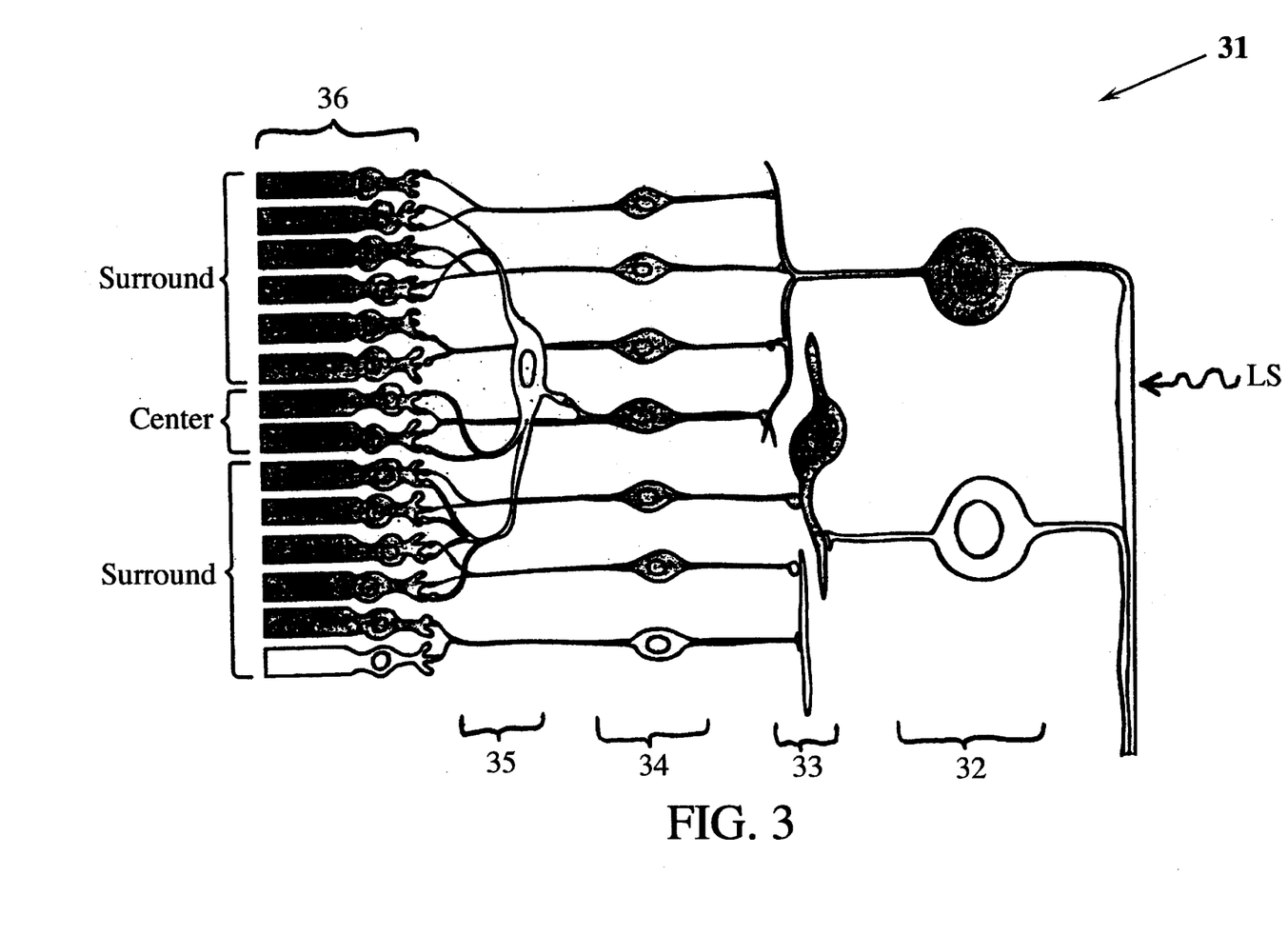
FIG. 3 is a schematic view of an active layer in a retina.

According to one widely held view of the human vision system, the retina 31 of a normally functioning eye is constructed as shown in the schematic view in FIG. 3, where incident light LS enters from the right, travels past (or through) arrays of ganglion cells 32, amacrine cells 33, bipolar cells 34 and horizontal cells 35 (collectively referred to herein as an "active layer") to a photoreceptor region 36 containing about 125 million rods and cones and initiates a visual process that will produce an image. The incident light is apparently not defocused or substantially altered in passing through the active layer. If the photoreceptors are functioning normally, the rods, with a first type of pigment, and the smaller number of cones, with second, third and fourth types of pigment, will respond to receipt of light in different wavelength segments of the spectrum and produce electromagnetic signals that are first received and processed by the array 34 of bipolar cells (for direct transfer to the array 32 of ganglion cells and to the array 33 of amacrine cells) and by the array 35 of horizontal cells (for indirect transfer). A ganglion cell sub-layer and a bipolar sub-layer in a human are estimated to have thickness ranges of about 10–30 $\mu$m and 30–50 $\mu$m, respectively.

Different photoreceptors respond affirmatively to the presence of light and to the absence of light, through depolarization and/or hyperpolarization of the corresponding cells. If some of the photoreceptors (as in color blindness) or most of the photoreceptors in a certain region of the retina (as in age-related macular degeneration) are not responding properly, receipt of the incident light at the photoreceptor sites produces an inadequate response that is not processed or is poorly processed by the cells in the active layer. The invention disclosed herein supplements, or compensates for, or bypasses the photoreceptor sites by delivering equivalent electrical signals to appropriate portions of the active layer, especially to cells in the bipolar sub-layer and/or in the ganglion sub-layer of the active layer.

Through a convergence process in a normally functioning retina, signals from many photoreceptors are received in a geometrically defined receptive field associated with a bipolar cell and/or with a horizontal cell. In turn, a bipolar cell and a horizontal cell will deliver its resulting signal, through another convergence process, to a ganglion cell (for direct transfer), or to an amacrine cell that interacts with a ganglion cell. The ganglion cell output signal is directed through the optical nerve to a visual information processing center of the brain.

Each receptive field in any of the four kinds of active layer cells has a central receptive region and an annular surround receptive region that surrounds and is contiguous to the central region. A central receptive region and a surround receptive region of a cell may each receive a stimulatory signal and an inhibitory signal, depending upon the cell's construction. A bipolar cell tends to deliver its resulting signal to a central receptive region of a ganglion cell, and a horizontal cell tends to deliver its resulting signal to a surround receptive region of a ganglion cell, as part of the convergence process. Central and surround receptive regions and retinal processing are discussed by David Hubel in *Eye, Brain and Vision*, Scientific American Publ, New York, 1988, 1995, pp. 36–57, and in more detail in Neil R. Miller and Nancy J. Newman, *Walsh & Hoyt's Clinical Neuro-Ophthalmology*, Lippincott, Williams & Wilkins, Philadelphia, Fifth Ed., 1999, pp. 60–76.

Figure 4:
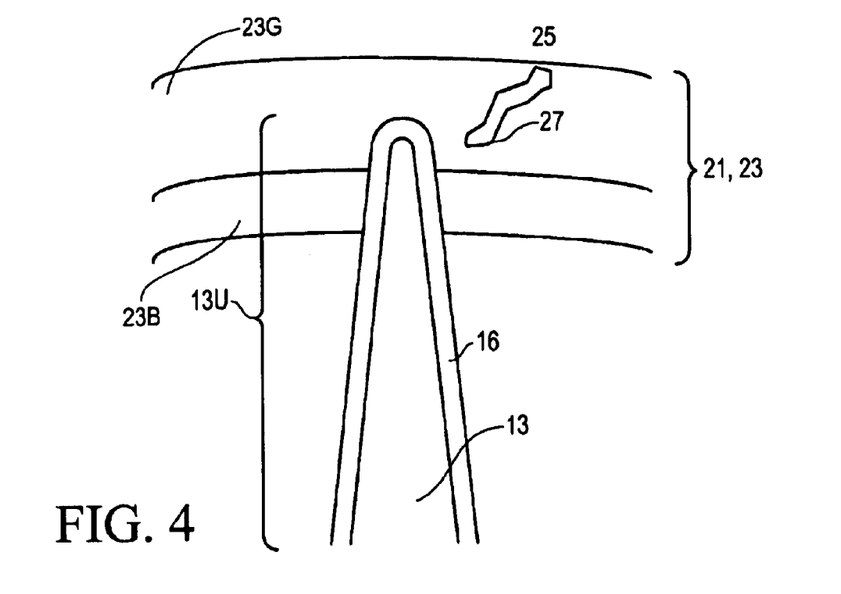
FIG. 4 is a schematic view of interaction between a protein-coated CNT tower tip and a neurite that transmits an optical signal in a retinal active layer.

In another embodiment, illustrated in FIG. 4, a selected portion of the first (exposed) end of a CNT tower can be coated with one or more selected proteins, growth factors and/or other biologically active substances 16 before an active layer of the retina is penetrated. If the first end 13U of the CNT tower 13 is located sufficiently close to an active optical signal processing site 25 in the active layer 23, a neurite 27 (analogous to an axon associated with a neuron in the brain) may be induced to grow toward the CNT tower first end 13U so that the CNT tower establishes a functional connection between a CCD pixel (not shown in FIG. 4) and the active layer of the retina. Suitable substances for coating the CNT tower include polylysine, collagen, fibronectin, laminin, brain-derived neurotrophic factor, ciliary neurotrophic factor, nerve growth factor, forskolin, inhibitors of myelin-associated glycoprotein and inhibitors of NOGO. NOGO, a member of the reticulon family of proteins, is an inhibitory myelin protein that prevents growth of neurons. NOGO occurs in three forms, NOGO-A, NOGO-B and NOGO-C, and the name "NOGO" refers collectively to all three forms. The growth of a neurite to contact a CNT tower provides a direct and closer connection of the active layer of the retina to the CNT tower, analogous to signaling pathways and connections that are established and maintained in a normally functioning eye.

Alternatively or additionally, a selected portion of the first end of each CNT tower, or the entire tower, can be chemically modified, to promote anchoring of the biologically active substance 16 on the CNT tower or for some related purpose. Suitable chemical modifications include hydrogenation (using H), nitrogenation (using N), addition of one or more carboxylic acid groups, and addition of one or more amine groups. Secondary chemical modifications (e.g., oxidization and reduction) may be performed to make the added chemical groups more reactive, or more selectively reactive, to permit subsequent chemical modification.

Figure 5:
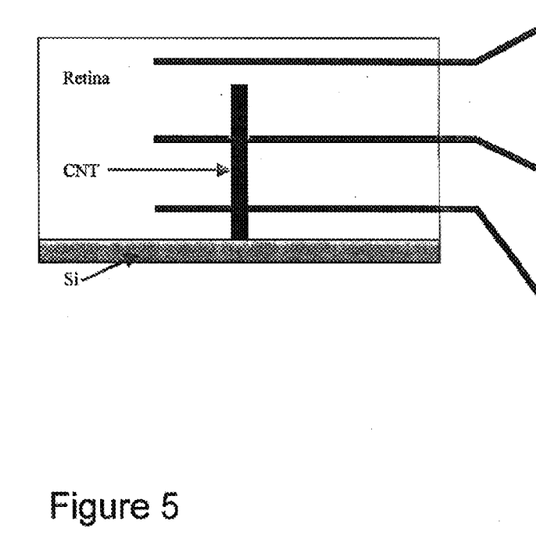
FIGS. 5A, 5B and 5C are sectional images of an active layer of a retina at three depths.
Figure 5A:
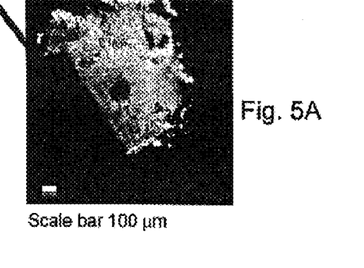
Figure 5B:
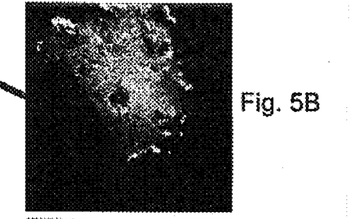
Figure 5C:
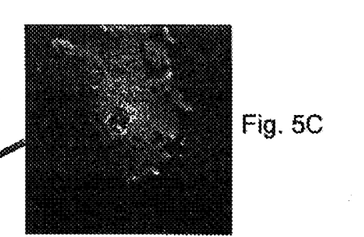

FIGS. 5A, 5B and 5C are sectional images of penetration of a retina formed at three approximate distances., d≈25 μm, d≈75 μm and d≈110 μm, measured from the surface of the silicon chip. Destruction of the tissue beyond the aperture through which the CNT tower passes is minimal or does not occur.

Figure 6:
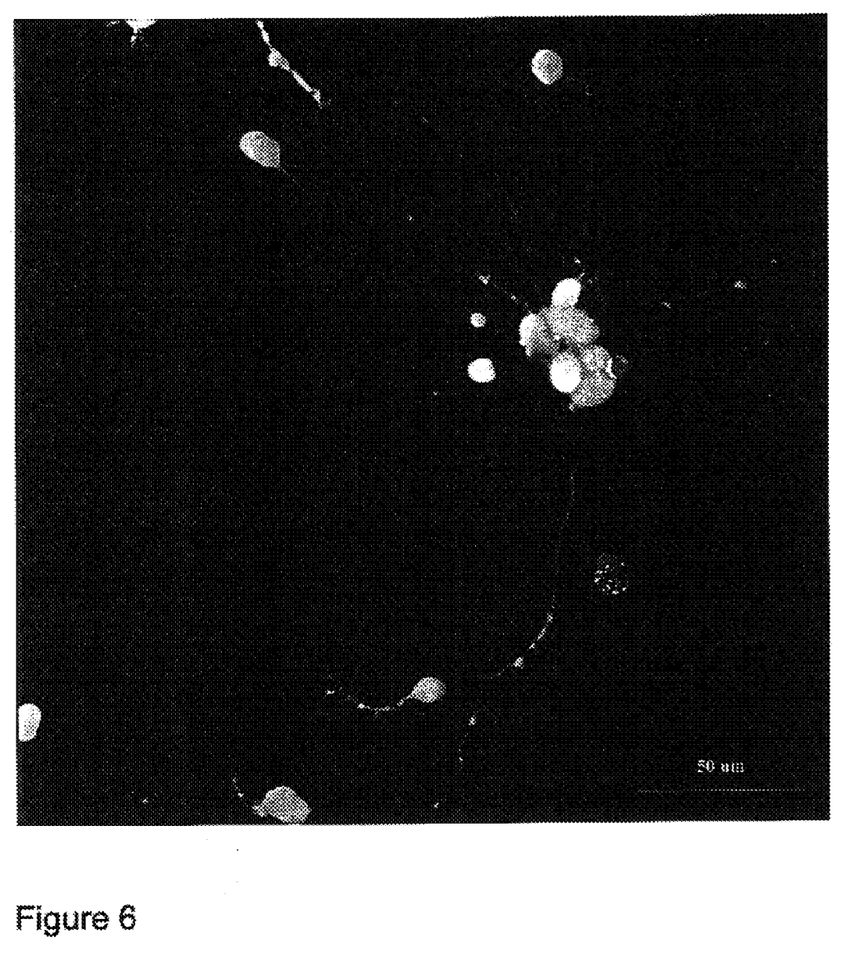
FIG. 6 is an image of retinal ganglion cells cultivated on a surface of CNT towers.

FIG. 6 is a fluorescence image of retinal ganglion cells that have been cultivated on a surface of CNT towers for three days. This indicates that the CNT tower material is biocompatible with retinal ganglion cells and that the ganglion cells are able to grow toward, not avoid, tips of CNT towers.

Figure 7A:
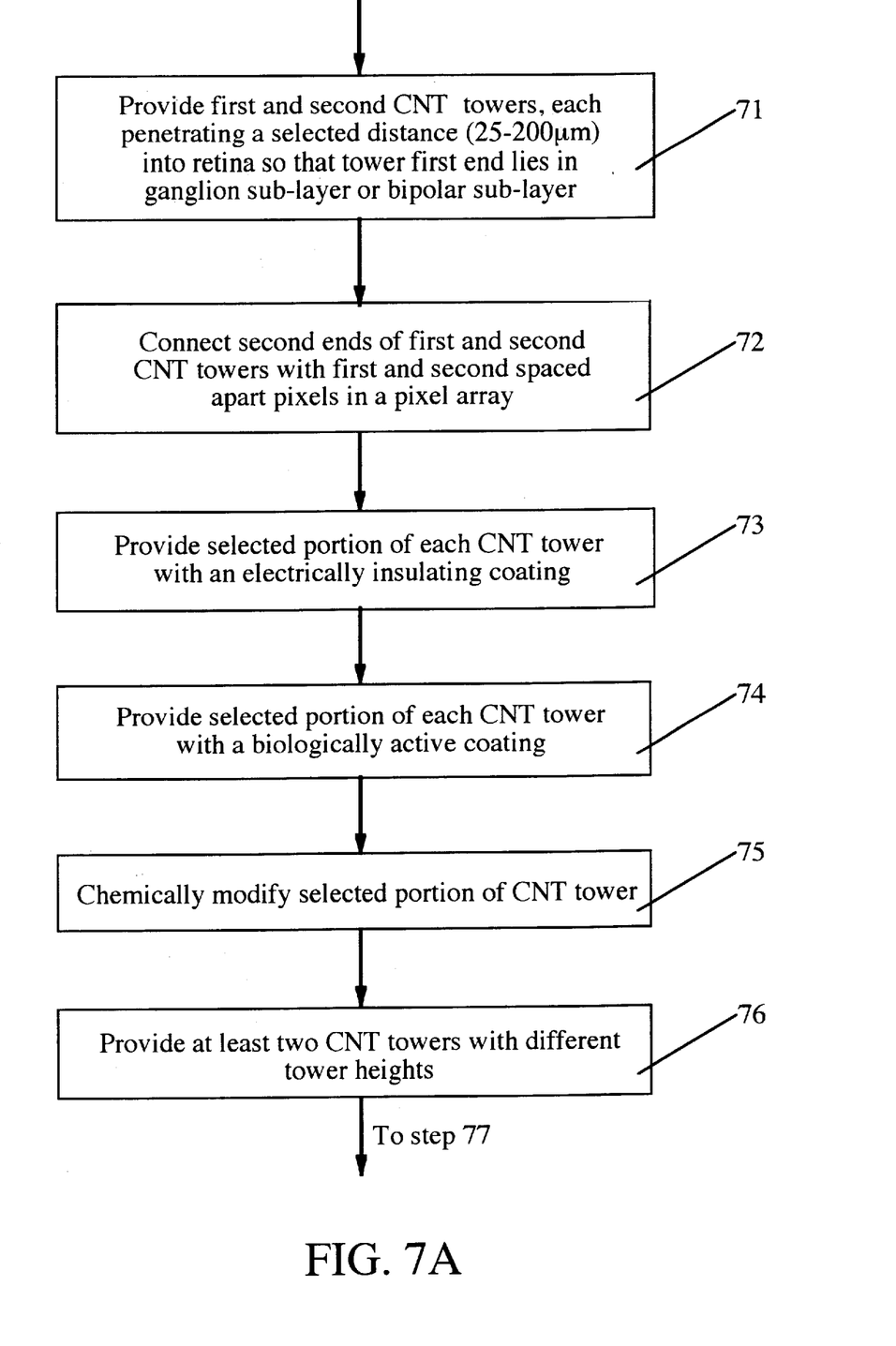
FIG. 7 is a flow chart of a method for practicing the invention.
Figure 7B:
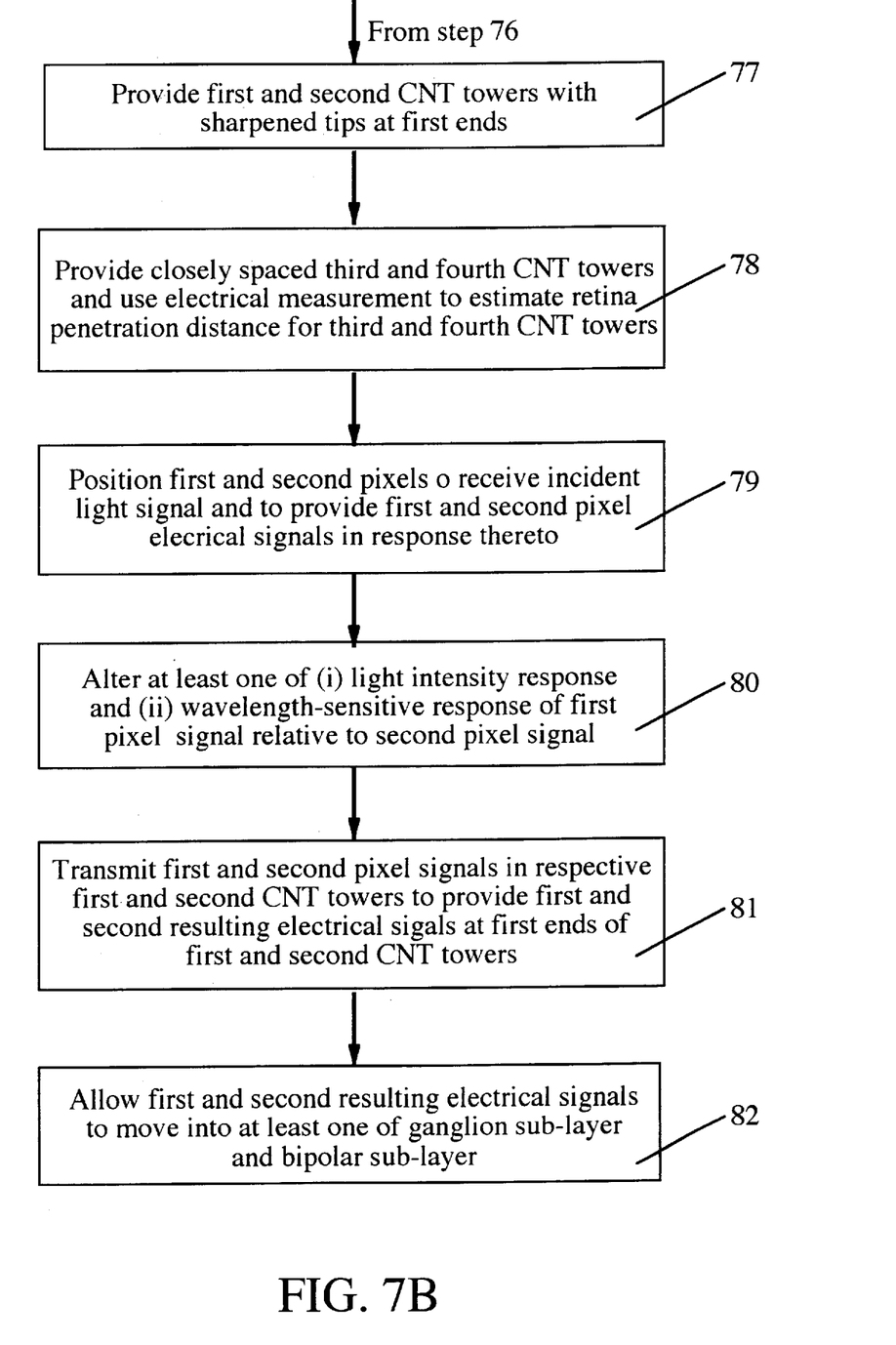

FIG. 7 is a flow chart of a procedure for practicing an embodiment of the invention. In step 71, at least first and second CNT towers are provided, with each tower including at least one CNT and having a height of at least 25–200 μm, adjacent to a retina of an animal, in a sub-retinal or epi-retinal location. Each tower is positioned so that a tip of a first end of each of the first and second CNT towers penetrates the retina a selected distance in a range of about 25–200 μm and the tip is located within at least one of a ganglion sub-layer and a bipolar sub-layer of the retina. In step 72, a second end of each of the first and second CNT towers is connected with at least first and second spaced apart, light-receiving pixels, respectively, in a photodetector array of pixels. In steps 73, 74 and 75, selected portions of the CNT towers are provided with electrically insulating coatings (optional) and biologically active coatings (optional), or are chemically modified (optional), respectively. In step 76, the first and second CNT towers are optionally provided with different tower heights. In step 77, tips of the first and second CNT towers are optionally sharpened. In step 78, closely spaced third and fourth CNT towers are optionally provided and an electrical measurement is used to estimate a CNT tower penetration distance for the third and fourth towers.

In step 79, the first and second pixels are positioned to receive first and second electromagnetic signals, respectively, from an incident light signal and to provide first and second pixel electrical signals, respectively, in response thereto. In step 80, at least one of a light intensity response and a wavelength-sensitive response for the first pixel signal is optionally altered relative to at least one of a light intensity response and a wavelength-sensitive response for the second pixel signal. In step 81, the first and second pixel electrical signals are transmitted via the first and second CNT towers, respectively, to provide first and second resulting electrical signals at the first ends of the first and second CNT towers. In step 82, the first and second resulting electrical signals are allowed to move into at least one of the ganglion layer and the bipolar layer in the retina.

CNT towers in an array can be provided at two or more different heights, relative to the surface of the catalyst used to grow the CNT towers. One method of accomplishing this is to provide two or more different catalyst layers in different (isolated) regions, where each catalyst promotes CNT tower growth to a different height. For example, relatively thin layers of Co or Ni or Fe will promote growths of different maximum heights of MWCNTs, and different thicknesses of a given catalyst will also promote growths of different maximum heights of MWCNTs. The different catalysts may be distributed in a "checkerboard array" of non-overlapping polygons, ovals or other geometric patterns. Where the position of the base layer of catalyst and support layer is controlled, different heights of CNT towers in an array will penetrate the active layer to different depths and thereby provide optical signal stimulations to different sub-layers within the active layer. Alternatively, arrays of CNT towers of different heights can be used to measure the normal or pathological electrical activity of different sub-layers within the active layer of the retina, in order to understand normal and pathological signal processing and signal integration.

Figure 8:
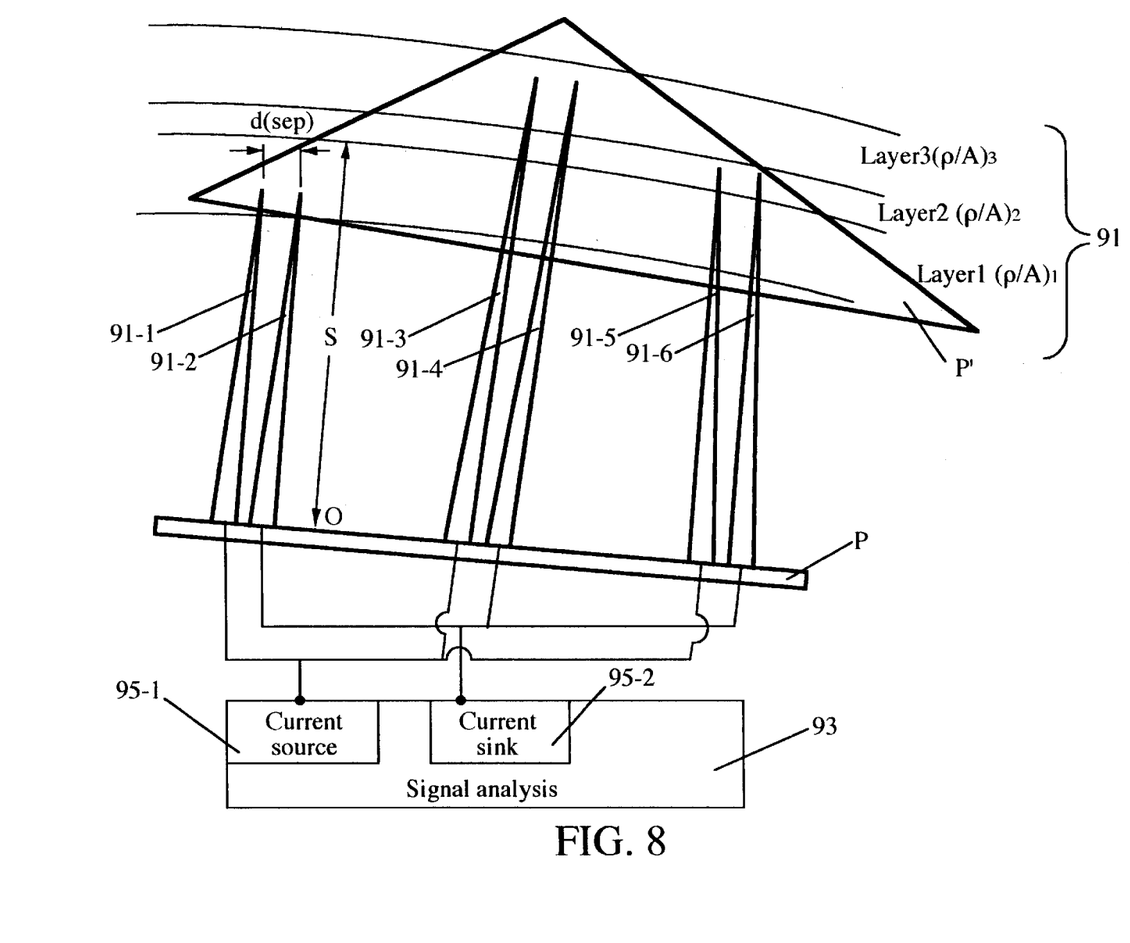
FIG. 8 illustrates methods for estimating a depth of penetration of a pair of CNT towers and for estimating angular orientation of a CNT tower array.

A depth of penetration of an array of CNT towers can be estimated using an approach illustrated in FIG. 8. One or more pairs, 91-1 and 91-2, of adjacent CNT towers of approximately equal height in an array 61 is dedicated to estimation of penetration distance, rather than to vision. Each dedicated pair, 91-1 and 91-2, is electrically connected to a signal analysis module 93 that includes an electrical current source 95-1 and an electrical current sink 95-2, respectively. The known distance of separation d(sep) of the CNT towers 91-1 and 91-2 is preferably at least 1–5 μm, but may be less than 1 μm in some circumstances.

As the array 91 of CNT towers penetrates the retina and the active layer, an electrical field of appropriate strength E is created between the two towers, 91-1 and 91-2, so that a small electrical current I is established and measured between these two CNT towers. The resistance, r=E/I, is then computed approximately by $$r = \rho \cdot d(\text{sep})/A, \quad (1)$$

where $\rho$ is the resistivity of the medium separating the two CNT towers and A is an effective cross-sectional area of the medium through which electrical charge flows from the first tower 91-1 to the second tower 91-2. The individual quantities, $\rho$ and A, may not be measurable, but a first ratio $\rho/A$ is measurable and will differ from one sub-layer (e.g., ganglion) to another sub-layer (e.g., bipolar) within the retina. By determining a second ratio $r/d(\text{sep})$, the first ratio $\rho/A$ is determined, and the subject can determine in which sub-layer the tips of the two towers, 91-1 and 91-2, are presently located. Penetration of the CNT tower array 91 proceeds until the computed first ratio $\rho/A$ has a value corresponding to the target sub-layer for the CNT tower tips.

By providing two or three spaced apart pairs, 91-1/91-2 and 91-3/91-4 and 91-5/91-6, of dedicated CNT towers, where each pair has a selected tower height, the angular orientation of the CNT tower array can be estimated. The height of the tips of each CNT tower pair is estimated, and an equation of a straight line or plane that passes through the two or three locations is determined, from which the angular orientation of the CNT tower array can be estimated. Assume, for example, that each of the first, second and third dedicated pairs of towers have $(x,y)$ Cartesian coordinates $(x_k, y_k)$ ($k=1, 2, 3$), measured in a plane of the catalyst layer P, and has an estimated tip height of the kth pair, measured from the plane P, of $z=z_k$. Parameters, $\alpha_x$, $\alpha_y$, $\alpha_z$ and s, of an equation $$\alpha_x \cdot x + \alpha_y \cdot y + \alpha_z \cdot z - s = 0, \quad (2)$$

of a plane P' passing through the three pairs of tips can be determined, using geometrical analysis. Here, $\alpha_x$, $\alpha_y$ and $\alpha_z$ are direction cosines for a normal to the plane P' and s is the perpendicular distance from a coordinate origin O on P to the plane P'. The angular orientation of the CNT tower array and the tower tip penetration depths are then determined from the parameters $\alpha_x$, $\alpha_y$, $\alpha_z$ and s and the locations of the three dedicated pairs of CNT towers.

A tip 13T (FIG. 1) of a CNT tower is preferably sharpened for easier penetration of the retina, to achieve a tip diameter that may range from 1 $\mu$m to 25 $\mu$m. This tip sharpening may be promoted by applying one or more of the following processes to the tips of selected CNT towers before implant of the CNT array: chemical etching, electron beam etching, ion beam etching, plasma etching, and short distance electrical arcing between selected tips and an adjacent electrically charged surface.

The system disclosed herein can be used to correct or compensate for many different deficiencies of the visual system of humans and other animals. Some humans suffer from age-related macular degeneration (AMD), whereby the central vision is severely compromised and, at best, limited peripheral vision remains. In many instances of AMD, the photoreceptors for central vision become non-functional but the active layer remains fully functional and ready to respond to signals produced by photoreceptors or their equivalent. The disclosed system replaces a compromised retinal photoreceptor system with an array of equivalent external photoreceptors (e.g., a CCD pixel array) and with an array of CNT towers that provide a pathway to transmit signals produced by the external photoreceptors to an active layer of a retina. One result can be partial or full restoration of central vision to an AMD sufferer.

Where a human or other animal manifests color blindness, it appears that at least one of the three kinds of photoreceptor cones in the eye either functions weakly or not at all. Assuming, for example, that the blue-sensitive cones are not responding, the system disclosed herein can be implanted and arranged to respond only to blue light, with a wavelength sensitivity in the blur region that approximately matches that of a non-color blind eye; response to red and green light by the external photoreceptor array is either attenuated or canceled optically or electronically. Here, the disclosed system is used to supplement a color blind animal's vision system to partly or fully restore wavelength sensitivity in the "missing" region(s).

Retinitis pigmentosa ("RP") refers to a group of progressively degenerative diseases of the visual system in which the rods and/or cones slowly degenerate. An early stage of RP is pronounced night blindness. Later stages may involve functional atrophy, pigment changes in the retina and/or marked constriction of the visual field. The disclosed system can compensate for the night blindness, by provision of a nonlinear response to light intensity.

Signal processing electronics associated with the photoreceptor array 19 (FIG. 1) optionally includes a signal altering mechanism that alters at least one of a light intensity signal or a wavelength sensitive signal provided by a first pixel relative to the corresponding signal provided by a second, spaced apart pixel, to correct or compensate for what would otherwise be inadequate responses of the eye to incident light.

The light-receiving array 19 can be located outside the retina 21, as shown in FIG. 1, and the CNT tower array system 11, can be located epi-retinally or sub-retinally.

What is claimed is:

1. A method for processing light signals received by the eye of a human or other animal, the method comprising:

providing at least first and second carbon nanotube ("CNT") towers, each including at least one carbon nanotube and having a height of at least 25–200 $\mu$m, adjacent to a retina of a subject, in a sub-retinal or epi-retinal location, and positioned so that a tip of a first end of each of the first and second CNT towers penetrates the retina a selected distance in a range of about 25–200 $\mu$m and the tip is located within at least one of a ganglion layer and a bipolar layer of the retina, where a second end of each of the first and second CNT towers is connected with at least first and second spaced apart, light-receiving pixels, respectively, in a photodetector array of pixels;

allowing the first and second pixels to receive first and second electromagnetic signals, respectively, from an incident light signal and to produce first and second pixel electrical signals, respectively, in response thereto;

allowing the first and second pixel electrical signals to be transported in the first and second CNT towers, respectively, and to provide first and second resulting electrical signals at the first ends of the respective first and second CNT towers; and allowing the first and second resulting electrical signals to move into at least one of the ganglion layer and the bipolar layer in the retina.

2. The method of claim 1, further comprising providing a selected portion of each of said first and second CNT towers, adjacent to but not including said tip of said first end of said tower, with an electrically insulating coating.

3. The method of claim 1, further comprising providing each of said first and second CNT towers as an array of at least two multi-walled carbon nanotubes.

4. The method of claim 1, further comprising providing each of said first and second CNT towers as an array of at least two carbon nanofibers.

5. The method of claim 1, further comprising providing a selected portion of each of said first and second CNT towers first end with a coating of a biologically active substance.

6. The method of claim 5, further comprising choosing said biologically active substance from a group of substances consisting of polylysine, collagen, fibronectin, laminin, brain-derived neurotrophic factor, ciliary neurotrophic factor, nerve growth factor, forskolin, inhibitors of myelin-associated glycoprotein and inhibitors of NOGO.

7. The method of claim 1, further comprising applying a selected chemical modification process to a selected portion of said first and second towers.

8. The method of claim 7, further comprising choosing said chemical modification process from a group of processes consisting of hydrogenation, nitrogenation, addition of at least one carboxylic acid group, and addition of at least one amine group.

9. The method of claim 1, further comprising providing a selected CNT growth catalyst and a selected metallic underlayer adjacent to said first and second CNT tower second ends.

10. The method of claim 9, further comprising providing said CNT growth catalyst from a group of catalysts consisting of Fe, Ni, Co, Mo and an alloy including at least two of Fe, Ni, Co and Mo.

11. The method of claim 9, further comprising providing said metallic underlayer from a group consisting of Al, Ir and an alloy including Al and Ir.

12. The method of system 9, further comprising providing first and second catalysts on first and second selected regions, respectively, of said underlayer, where the first and second catalysts promote growth of said CNT towers thereon with substantially different first and second tower heights, respectively.

13. The method of claim 1, further comprising providing said tips of said first and second CNT towers with sharpened ends having tip diameters lying in a range of 1–25 $\mu$m.

14. The method of claim 13, further comprising providing said sharpened tips by applying a tip alteration process drawn from the group of processes consisting of chemical etching, electron beam etching, ion beam etching, plasma etching and short distance electrical arcing between said a selected CNT tower tip and an adjacent electrically charged surface.

15. The method of claim 1, further comprising:
providing third and fourth CNT towers having tower tips and being spaced apart a selected small separation distance;
causing the third and fourth tower tips to penetrate said retina by substantially the same distance;
providing a selected voltage difference between the third and fourth tower tips and measuring an electrical current that results from the voltage difference;
estimating an electrical resistance of a region of said retina in which the third and fourth tower tips are located from the voltage difference and the measured electrical current; and
estimating a parameter value associated with the electrical resistance that is characteristic of the region of said retina in which the third and fourth tower tips are located, and estimating the penetration distance of the third and fourth tower tips into said retina according to the value of the estimated parameter.

16. The method of claim 1, further comprising receiving said first and second electromagnetic signals at said first and second pixels, respectively, and altering at least one of a light intensity response and a wavelength sensitive response of said first pixel signal relative to said second pixel signal before said first and second pixel signals are transmitted via said first and second CNT towers.

17. The method of claim 16, further comprising said at least one of said light intensity response and said wavelength sensitive response of said first signal relative to said second signal to partly or fully compensate for at least one of the following conditions of said subject's eye: age-related macular degeneration, color blindness and retinitis pigmentosa.

18. A system for processing light signals received by the eye of a human or other animal, the system comprising:
a photodetector array of light-receiving pixels, where at least first and second pixels produce first and second pixel electrical signals, respectively, in response to receipt by the at least first and second pixels of first and second electromagnetic signals from light incident on the at least first and second pixels;
at least first and second carbon nanotube ("CNT") towers, each including at least one carbon nanotube and having a height of at least 25–200 $\mu$m, positioned adjacent to a retina of a subject, in a sub-retinal or epi-retinal location, so that a tip of a first end of each of the at least first and second CNT towers penetrates the retina a selected distance in a range of 25–200 $\mu$m and the exposed end is located within at least one of a ganglion layer and a bipolar layer of the retina, where a second end of each of the at least first and second CNT towers is connected with the at least first and second pixels, respectively, in the photodetector array,
whereby each of the at least first and second pixels receives an electromagnetic signal from a light source and produces at least first and second pixel electrical signals, respectively, in response thereto, the at least first and second pixel signals are transmitted via the at least first and second CNT towers, respectively, to provide first and second resulting electrical signals at the first end of the respective first and second CNT towers, and the first and second resulting electrical signals move into at least one of the ganglion layer and the bipolar layer in the retina.

19. The system of claim 18, wherein a selected portion of each of said first and second CNT towers, adjacent to but not including said tip of said first end of said tower, has an electrically insulating coating.

20. The system of claim 18, wherein each of said first and second CNT towers comprises an array of at least two multi-walled carbon nanotubes.

21. The system of claim 18, wherein each of said first and second CNT towers comprises an array of at least two carbon nanofibers.

22. The system of claim 18, wherein a selected portion of each of said first and second CNT towers first end is coated with a biologically active substance.

23. The system of claim 22, wherein said biologically active substance is chosen from a group of substances consisting of polylysine, collagen, fibronectin, laminin, brain-derived neurotrophic factor, ciliary neurotrophic factor, nerve growth factor, forskolin, inhibitors of myelin-associated glycoprotein and inhibitors of NOGO.

24. The system of claim 18, wherein a selected chemical modification process is applied to a selected portion of said first and second towers.

25. The system of claim 24, wherein said chemical modification process is chosen from a group of processes consisting of hydrogenation, nitrogenation, addition of at least one carboxylic acid group, and addition of at least one amine group.

26. The system of claim 18, further comprising a selected CNT growth catalyst and a selected metal underlayer positioned adjacent to each of said first and second CNT tower second ends.

27. The system of claim 26, wherein said CNT growth catalyst is drawn from a group of catalysts consisting of Fe, Ni, Co, Mo and an alloy including at least two of Fe, Ni, Co and Mo.

28. The system of claim 26, wherein said metal underlayer is drawn from a group consisting of Al, Ir and an alloy including Al and Ir.

29. The system of system 26, wherein selected first and second catalysts are provided on first and second selected regions, respectively, of said underlayer, where the first and second catalysts promote growth of said CNT towers thereon with substantially different first and second tower heights, respectively.

30. The system of claim 18, wherein said tips of said first and second CNT towers are provided with sharpened ends having tip diameters lying in a range of 1–25 $\mu$m.

31. The system of claim 30, wherein said sharpened tips are provided by applying a tip alteration process drawn from the group of processes consisting of chemical etching, electron beam etching, ion beam etching, plasma etching and short distance electrical arcing between said a selected CNT tower tip and an adjacent electrically charged surface.

32. The system of claim 18, further comprising third and fourth CNT towers having tower tips and being spaced apart a selected small separation distance, where the third and fourth tower tips penetrate said retina by substantially the same distance;

a source of a selected voltage difference between the third and fourth tower tips; and a current measurement and analysis mechanism for measuring an electrical current between the third and fourth tower tips that results from the voltage difference, and that estimates an electrical resistance of a region of said retina in which the third and fourth tower tips are located from the voltage difference and the measured electrical current, whereby a parameter value associated with the electrical resistance is estimated that is characteristic of the region of said retina in which the third and fourth tower tips are located, and the penetration distance of the third and fourth tower tips into said retina is estimated according to the value of the estimated parameter.

33. The system of claim 18, wherein said first and second electromagnetic signals are received at said first and second pixels, respectively, and at least one of a light intensity response and a wavelength sensitive response of said first pixel signal relative to said second pixel signal is altered before said first and second pixel signals are transmitted via said first and second CNT towers.

34. The system of claim 33, wherein said at least one of said light intensity response and said wavelength sensitive response of said first signal is altered relative to said second signal to partly or fully compensate for at least one of the following conditions of said subject's eye: age-related macular degeneration, color blindness and retinitis pigmentosa.

* * * * *